United States Patent [19]

Bader et al.

[11] Patent Number: 5,185,454
[45] Date of Patent: Feb. 9, 1993

[54] PROCESS FOR THE PREPARATION OF SYMMETRICAL DIARYLACETYLENES

[75] Inventors: Axel Bader, Bergisch Gladbach; Dieter Arlt, Cologne, both of Fed. Rep. of Germany

[73] Assignee: Bayer Aktiengesellschaft, Leverkusen, Fed. Rep. of Germany

[21] Appl. No.: 594,265

[22] Filed: Oct. 2, 1990

[30] Foreign Application Priority Data

Nov. 1, 1989 [DE] Fed. Rep. of Germany ....... 3936297

[51] Int. Cl.[5] .................. C07C 2/00; C07D 307/77
[52] U.S. Cl. .................. 549/240; 549/241; 549/246; 558/359; 560/64; 560/73; 562/405; 562/488; 564/155; 568/34; 568/316; 568/636; 568/646; 568/660; 568/729; 568/932; 570/128; 570/143; 570/184; 585/534
[58] Field of Search .................. 549/241, 240, 246; 585/534; 558/359; 568/316, 636, 646, 660, 34, 729, 932; 560/64, 73; 570/178, 143, 184; 562/405, 199, 360; 564/155

[56] References Cited

U.S. PATENT DOCUMENTS 4,223,172 9/1980 Sabourin et al. .................. 568/812
4,973,707 11/1990 Nye ..................... 549/241

FOREIGN PATENT DOCUMENTS 0050428 9/1981 European Pat. Off. .

OTHER PUBLICATIONS

Morrison & Boyd, *Organic Chemistry* 3rd ed., 1974, p. 260.
Tetrahedron letters No. 50, pp. 4467–4470, 1975 Pergamon Press Printed in Great Britain.
Houben-Weyl, XIII 19b (1984) pp. 987–994.
Houben-Weyl, V/2a (19n) pp. 563–564.
Houben-Weyl, V/2a (1977) pp. 33–51, pp. 52–53.

*Primary Examiner*—C. Warren Ivy
*Assistant Examiner*—Raymond Covington
*Attorney, Agent, or Firm*—Sprung Horn Kramer & Woods

[57] ABSTRACT

Symmetrical diaryl-acetylenes can be prepared by reacting an aryl halide with acetylene in the presence of a palladium catalyst and a base. If the acetylene is introduced into the liquid reaction mixture using a high intensity gas dispersion means, the aryl halide used can be an aryl bromide.

18 Claims, No Drawings

PROCESS FOR THE PREPARATION OF SYMMETRICAL DIARYLACETYLENES

BACKGROUND OF THE INVENTION

1. Field of the Invention

The present invention relates to a process for the preparation of symmetrical diaryl-acetylenes from aryl bromides and acetylene in the presence of a palladium catalyst and a base, the acetylene being introduced into the liquid reaction mixture using a high intensity gas dispersion means.

Symmetrical diaryl-acetylenes are valuable intermediates. For instance, diaryl-acetylenes of the type which carry, on each of the aryl radicals, a carboxyl, carboxylic ester or carbonyl halide group or a group which can be converted into a carboxyl group, an ester group or a carbonyl halide group, are partially hydrogenated at the triple bond and the resulting bifunctional diaryl-olefin can be converted by polycondensation to give a high temperature-resistant material.

2. Description of the Related Art

Diaryl-acetylenes can be prepared, for example, by dehydrohalogenation of diaryl-halogenoalkenes or by two-fold dehydrohalogenation of vic- or gem- diaryl-dihalogenoalkanes using strong bases under relatively severe reaction conditions (Houben-Weyl, Methoden der Organischen Chemie, Volume V/2a (1977), p. 53 et seq.). These reactions are not suitable for the preparation of diaryl-acetylenes containing groups which are sensitive to bases. Furthermore, the halogen compounds used as starting material are often difficult to obtain.

Another method for the preparation of symmetrical diaryl-acetylenes is the Castro-Stephans reaction (loc. cit., p. 563 et seq.). In this reaction, copper acetylides are reacted with aryl iodides in boiling pyridine to give disubstituted acetylenes. This multistage process is confined to using the relatively expensive and often poorly accessible aryl iodides to achieve acceptable yields.

Moreover, diaryl-acetylenes can be prepared starting from aryl iodides or aryl bromides and aryl acetylenes using palladium catalysis (Houben-Weyl, volume XIII/9b (1984), p. 987 et seq.). However, the aryl acetylenes required for this preparation can only be obtained at great expense in multi-stage processes.

Furthermore, it is known that diaryl-acetylenes can be prepared by reacting acetylene with halogen compounds in the presence of bis(triphenylphosphine)palladium dichloride and copper(I) iodide in solution in diethylamine (Tetrahedron Lett. (1975), 4467). Suitable halogen compounds for this reaction are bromoalkenes or bromopyridine; in the benzene series, this reaction is limited to aryl iodides. The reaction is carried out by introducing acetylene through a delivery tube for 6 hours into the stirred solution of a batch of 10 mmol of iodobenzene.

SUMMARY OF THE INVENTION

Surprisingly, it has now been found that by intensively dispersing acetylene into the liquid reaction mixture, it is possible to employ the more stable, easier-to-prepare and consequently less expensive aryl bromides instead of the aryl iodides and, at the same time, to accelerate the reaction even in relatively large batches (higher space-time yield). Consequently, this reaction is also suitable for industrial applications, for example for the use given above.

The present invention accordingly provides a process for the preparation of symmetrical diaryl-acetylenes of the formula

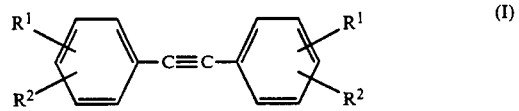

in which
R$^1$ is hydrogen, straight-chain or branched C$_1$–C$_8$-alkyl, C$_3$–C$_8$-cycloalkyl, phenyl, C$_7$–C$_{10}$-aralkyl, straight-chain or branched C$_1$–C$_8$-alkoxy, phenoxy, benzyloxy, β-phenyl-ethenyl, phenyl-ethinyl, phenyl-sulphonyl, phenyl-carbonyl, hydroxyl in free or protected form, fluorine, chlorine, nitro, cyano, COR$^3$, NR$^4$R$^5$ or CONR$^4$R$^5$ and R$^2$ represents hydrogen, straight-chain or branched C$_1$–C$_8$-alkyl, fluorine, chlorine, cyano, COR$^3$ or CONR$^4$R$^5$ and R$^1$ and R$^2$, if they are adjacent, may together form a dicarboxylic acid anhydride group,
where
R$^3$ is hydrogen, hydroxyl, straight-chain or branched C$_1$–C$_8$-alkyl, straight-chain or branched C$_1$–C$_8$-alkoxy, phenyl or phenoxy and R$^4$ and R$^5$, independently of one another, represent hydrogen or, straight-chain or branched C$_1$–C$_8$-alkyl and R$^4$ may also be C$_2$–C$_4$-alkoxycarbonyl or C$_2$–C$_4$-acyl, and furthermore R$^4$ and R$^5$ may together form C$_4$–C$_8$-alkylene, and it being possible for the benzene rings in the radicals R$^1$ and R$^2$ for their part to be substituted by straight-chain or branched C$_1$–C$_8$-alkyl, straight-chain or branched C$_1$–C$_8$-alkoxy, fluorine, chlorine or COR$^3$, by reaction of an aryl halide with acetylene in the presence of a palladium catalyst and a base, characterized in that the acetylene is introduced into the liquid reaction mixture using a high intensity gas dispersion means and the aryl halides used are aryl bromides of the formula

in which
R$^1$ and R$^2$ are as defined above.

DETAILED DESCRIPTION OF THE INVENTION

Examples of straight-chain or branched C$_1$–C$_8$-alkyl are methyl, ethyl, propyl, isopropyl, butyl, isobutyl, tert.-butyl, and the isomeric amyls, hexyls and octyls. Among these compounds, preference is given to the above-mentioned C$_1$–C$_4$-alkyls, and particular preference is given to methyl and ethyl.

Examples of C$_3$–C$_8$-cycloalkyl are cyclopropyl, methyl-cyclopropyl, dimethyl-cyclopropyl, tetramethylcyclopropyl, cyclobutyl, cyclopentyl, methylcyclopentyl, cyclohexyl, methyl-cyclohexyl, cycloheptyl and cyclooctyl. Among these compounds, preference is given to cyclopropyl, cyclopentyl and cyclohexyl and also to their mono- or poly-methyl-substituted derivatives.

Examples of $C_7$-$C_{10}$-aralkyl are benzyl, α- or β-phenyl-ethyl, α-, β- or γ-phenyl-propyl and -isopropyl; among these compounds, preference is given to benzyl.

Examples of straight-chain or branched $C_1$-$C_8$-alkoxy are methoxy, ethoxy, propoxy, isopropoxy, butoxy, isobutoxy, tert.-butoxy, and the isomeric amyls, hexyls and octyls. Among these compounds preference is given to the abovementioned $C_1$-$C_4$-alkoxy groups, and particular preference is given to methoxy and ethoxy.

Hydroxyl as $R^1$ may be present in free or protected form. Suitable protected forms are the esterified or etherified form from which the free form can be obtained again. Examples of the esterified form are the acetyl or propionyl esters; examples of the etherified form are the tetrahydropyranyl ethers, the trialkylsilyl ethers or the tert.-alkyl ethers.

If the radicals $R^4$ and $R^5$ together form $C_4$-$C_8$-alkylene, the corresponding amine substituents are derived from cyclic bases such as pyrrolidine, piperidine, azacyclohexane or aza-cyclooctane.

The aryl bromides used are preferably those of the formula

in which
R$^{11}$ is hydrogen, straight-chain or branched $C_1$-$C_8$-alkyl, phenyl, benzyl, straight-chain or branched $C_1$-$C_8$-alkoxy, phenoxy, benzyloxy, β-phenyl-ethenyl, phenyl-sulphonyl, phenyl-carbonyl, fluorine, chlorine, nitro, cyano, COR$^{13}$ or NR$^{14}$R$^{15}$ and
R$^{12}$ represents hydrogen, straight-chain or branched $C_1$-$C_8$-alkyl, fluorine, chlorine, cyano or COR$^{13}$ and
R$^{11}$ and R$^{12}$, if they are adjacent, may together form a dicarboxylic acid anhydride group,
where
R$^{13}$ is hydrogen, hydroxyl, straight-chain or branched $C_1$-$C_4$-alkyl or straight-chain or branched $C_1$-$C_4$-alkoxy and
R$^{14}$ and R$^{15}$, independently of one another, represent hydrogen or straight-chain or branched $C_1$-$C_4$-alkyl and R$^{14}$ may also be $C_2$-$C_4$-acyl and, moreover, R$^{14}$ and R$^{15}$ may together form $C_4$-$C_8$-alkylene, and
it being possible for the benzene rings in the radicals R$^{11}$ and R$^{12}$ for their part to be substituted by straight-chain or branched $C_1$-$C_4$-alkyl, straight-chain or branched $C_1$-$C_4$-alkoxy, fluorine, chlorine or COR$^{13}$.

The aryl bromides used are particularly preferably those of the formula

in which
R$^{21}$ is hydrogen, straight-chain or branched $C_1$-$C_4$-alkyl, phenyl, β-phenyl-ethenyl, phenyl-sulphonyl, phenyl-carbonyl, fluorine, chlorine, cyano or COR$^{23}$ and
R$^{22}$ represents hydrogen, methyl, ethyl, cyano or COR$^{23}$ and
R$^{21}$ and R$^{22}$, if they are adjacent, may together form a dicarboxylic acid anhydride group,
where
R$^{23}$ is hydrogen, hydroxyl, methyl, ethyl, methoxy or ethoxy and it being possible for the benzene rings in the radical R$^{21}$ for their part to be substituted by fluorine, chlorine or COR$^{23}$.

The following aryl bromides are listed by way of example for the process according to the invention: bromobenzene, 2-, 3- or 4-carboxy-bromobenzene, 2-, 3- or 4-formyl-bromobenzene, the various isomeric chloro-bromobenzenes, fluoro-bromobenzenes, chloro-fluoro-bromobenzenes, dichloro-bromobenzenes, difluoro-bromobenzenes, bromotoluenes, bromoxylenes, bromobenzenedicarboxylic acids, methyl (propyl, butyl etc.) esters of bromobenzenedicarboxylic acids, 2-, 3- or 4-bromobenzonitrile, 3- or 4-bromophthalodinitrile, 3- or 4-bromophthalic anhydride, ethyl 3- or 4-bromobenzoate, 3-methyl (or -ethyl)-4-carboxybromobenzene, 3-carboxy-4-methyl (or -ethyl)-bromobenzene, 2-, 3- or 4-bromoacetophenone, 3-bromo-6-methylacetophenone, 2-methyl (or -ethyl)-4-bromoacetophenone, 4-bromo-4'-fluorodiphenyl sulphone, 4-bromo-4'-chlorodiphenyl sulphone, 4-bromo-3'-fluorodiphenyl sulphone, 4-bromo-3'-chlorodiphenyl sulphone, 3-bromo-4'-fluorodiphenyl sulphone, 3-bromo-3'-fluorodiphenyl sulphone, 3-bromo-4'-chlorodiphenyl sulphone, 3-bromo-3'-chlorodiphenyl sulphone, 4-bromo-4'-carboalkoxy(methoxy, ethoxy etc.)stilbenes, 4-bromo-3'-carboalkoxy(methoxy, ethoxy etc.)stilbenes, 3-bromo-4'-carboalkoxystilbene, 3-bromo-3'-carboalkoxystilbenes, 4-bromo-4'-carboxystilbene, 4-bromo-3'-carboxystilbene, 3-bromo-4'-carboxystilbene, 3-bromo-3'-carboxystilbene, 4-bromo-4'-fluorobenzophenone, 4-bromo-4'-chlorobenzophenone, 4-bromo-3'-fluorobenzophenone, 4-bromo-3'-chlorobenzophenone, 3-bromo-4'-fluorobenzophenone, 3-bromo-4'-chlorobenzophenone, 3-bromo-3'-fluorobenzophenone, 3-bromo-3'-chlorobenzophenone, 4-bromo-4'-carboxybenzophenone, 4-bromo-4'-carboalkoxy(methoxy, ethoxy etc.) benzophenones, 4-bromo-4'-carboxybiphenyl, 4-bromo-4'-carboalkoxy(methoxy, ethoxy etc.)biphenyls, 4-acetyl-4'-bromobiphenyl, 4-acetyl-3'-bromobiphenyl.

The process according to the invention is carried out in the presence of a palladium catalyst. This palladium catalyst may also be composed of a mixture of a plurality of the palladium compounds listed below. However, preference is given in particular to the use of only one of the listed palladium compounds owing to the greater ease of working up and re-use. Examples of suitable palladium catalysts of this type are as follows: palladium black, palladium on carbon, simple inorganic and organic palladium salts, complexed inorganic and organic palladium salts, the complexing agents being nitriles such as benzonitrile, or a $C_1$-$C_4$-alkyl nitrile such as acetonitrile, triphenylarsine, or a phosphine which is characterized in more detail below, or else phenyl-palladium-diphosphine chloride (bromide, iodide) or palladium-tetraphosphines, likewise in these cases the phosphine which is characterized in more detail below being used, and also di-(dibenzylidene-acetone) palladium (=(dbe)$_2$Pd)or di-(1,1-bis[dibenzylphosphine]-ferrocene)palladium dichloride, dibromide or diiodide (=(dppf)₂PdCl₂(Br₂,I₂)).

Examples of simple inorganic and organic palladium salts are the chloride, the bromide, the iodide, the nitrate, the sulphate, the acetate, the propionate, preferably the abovementioned halides and the acetate. These salts may also be complexed with the abovementioned complexing agents, in the case of the phosphines suitable complexing agents being those of the formula $$P(R^6R^7R^8) \qquad (V)$$

in which

R⁶, R⁷ and R⁸, independently of one another, are straight-chain or branched $C_1$-$C_4$-alkyl or phenyl, it being possible for phenyl to be substituted by straight-chain or branched $C_1$-$C_4$-alkyl or $C_1$-$C_4$-alkoxy or by fluorine, chlorine or bromine.

The abovementioned palladium compounds can be formulated as follows: Pd, Pd black, Pd/C, PdX₂ (X=abovementioned anion), (C₆H₅-CN)₂PdX₂, (C₁-C₄-CN)₂PdX₂, (As[C₆H₅]₃)PdX₂, (PR⁶R⁷R⁸)₂PdX₂, C₆H₅PdI(PR⁶R⁷R⁸)₂, Pd(PR⁶,R⁷,R⁸)₄, (dbe)₂Pd and (dppf)₂PdHal₂. In this context, the preferred palladium catalysts are the abovementioned organic palladium salts, the complexed inorganic and organic palladium salts in which the complexing agent is a phosphine of the abovementioned type, and palladium-tetraphosphine containing a phosphine of the abovementioned type.

However, this list of abovementioned palladium compounds is incomplete. Other palladium compounds may likewise be used in the process according to the invention by a person skilled in the art following simple tests. All of these palladium compounds are known to a person skilled in the art.

The palladium catalyst (one or more Pd compounds) is used in an amount of 0.0005-5 mol %, preferably 0.05-2 mol %, relative to the aryl bromide.

It may be desirable and is consequently a preferred variant of the process according to the invention to activate the palladium catalyst by adding one or more phosphines of the formula (V), a phosphine of this type being used in an amount of 100-2000 mol %, relative to the palladium catalyst used.

It may also be desirable and is a further preferred variant of the process according to the invention to add to the palladium catalyst one or more copper salt(s) as cocatalyst in an amount of 50-1000 mol %, relative to the palladium catalyst. Suitable copper salts of this type are preferably copper halides (chlorides, bromides or iodides of Cu(I) or Cu(II)) or copper acetate. Particular preference is given to the use of Cu(I) iodide or Cu(II) acetate monohydrate.

A large number of compounds which are known to a person skilled in the art are suitable as a base in the process according to the invention. In principle, these compounds can be used singly or as a mixture of a plurality thereof; preference is given to the use of only one of the basic compounds for reasons of simplified reaction control, simplified working up and, if appropriate, simplified recycling. Examples of basic compounds are: the hydrides, hydroxides, oxides or amides of the alkali metals or alkaline earth metals. Suitable alkali metals or alkaline earth metals in this context are: lithium, sodium, potassium, rubidium, caesium, magnesium, calcium, strontium or barium, preferably lithium, sodium, potassium or calcium. Other suitable bases are the straight-chain or branched $C_1$-$C_8$-alcoholates of the abovementioned alkali metals or alkaline earth metals, the $C_1$-$C_8$-alkoxy radical corresponding to that described in more detail above. Other suitable basic compounds are nitrogen bases of the formula $$N(R^9R^{10}R^{16}) \qquad (VI)$$

in which

R⁹ and R¹⁰, independently of one another, are straight-chain or branched $C_1$-$C_8$-alkyl or else the two together are $C_4$-$C_8$-alkylene, it being possible in the alkylene chain for one carbon atom to be replaced by an oxygen atom or the group —NR¹⁶—, and R¹⁶ is hydrogen or straight-chain or branched $C_1$-$C_4$-alkyl.

Other suitable bases are bicyclic nitrogen compounds such as, for example, triethylenediamine, (diaza-bicyclo-octane=DABCO), diaza-bicyclo-nonene (DBN) or diaza-bicyclo-undecene (DBU).

Preferred bases for the process according to the invention are NaH, KH, CaH₂, LiNH₂, NaNH₂, KNH₂, Ca(NH₂)₂, DABCO, DBN, DBU or a nitrogen base of the formula $$N(R^{19}R^{20}R^{17}) \qquad (VII)$$

in which

R¹⁹ and R²⁰ together are $C_4$-$C_8$-alkylene, it being possible in the alkylene chain for one carbon atom to be replaced by an oxygen atom or the group —NR¹⁷—, and R¹⁷ is hydrogen, methyl or ethyl.

Examples of nitrogen bases of the formula (VI) in the case in which R⁹ and R¹⁰ together are $C_4$-$C_8$-alkylene, it being possible in the alkylene chain for one carbon atom to be replaced by an oxygen atom or the group —NR¹⁶—, are: pyrrolidine, piperidine, piperazine, morpholine, pyrrolidine, aza-cycloheptane, aza-cyclooctane.

Examples of particularly preferred bases are the nitrogen bases of the formula (VII) and also DABCO, DBN and DBU or a mixture of a plurality thereof.

The bases are used according to the invention in an amount of 80-600 mol %, preferably 95-400 mol %, relative to the aryl bromide.

The process according to the invention is carried out at a temperature of 0°-160° C., preferably at 50°-150° C.

If the aryl bromide which is to be used is not a liquid, the process according to the invention employs a solvent. Suitable solvents (diluents) are: hydrocarbons, in particular aromatic hydrocarbons such as benzene, toluene or xylene; ethers such as tetrahydrofuran, dioxane, ethylene glycol dimethyl ether or diethylene glycol dimethyl ether; alcohols such as methanol, ethanol or propanol; chlorinated hydrocarbons such as chloroform or chlorobenzene; nitriles such as acetonitrile, propionitrile or benzonitrile; amides such as dimethyl formamide (DMF), N-methyl-pyrrolidone (NMP) or hexamethylphosphoric acid triamide (HMPT); sulphoxides such as dimethyl sulphoxide (DMSO). Preference is given to the use as solvent (diluent) of one or more of the group comprising aromatic hydrocarbons, nitriles, amides or sulphoxides. Suitable amounts are 80-2000% by weight, preferably 100-1000% by weight, relative to the amount of aryl bromide. Another suitable solvent (diluent) is excess base of the abovementioned type, as long as this is a liquid. In this case, the amount of liquid base used exceeds the amount given further above in mol % and extends up to the amount by weight just given. It is advantageous to use a solvent (diluent) of this type even in the case of liquid aryl bromides.

In particular, the process according to the invention is characterized by means the use of a high intensity gas dispersion means by means of which the acetylene is introduced into the liquid reaction mixture. A high intensity gas dispersion means of this type can, for example, be a surface aerator, or a volume aerator such as a centrifugal aerator, a drum aerator, a water jet aerator, a submerged jet aerator, a tubular stirrer, a stirrer having a separate gas feed, a dip aerator, a sinter, a perforated baseplate or a static mixer or a two-fluid nozzle, through which the reaction mixture and the acetylene are simultaneously passed. Preference is given to the use of a volume aerator. This is particularly preferably a tubular stirrer. Furthermore, it can be advantageous to supplement the high intensity gas dispersion means with an additional mixer for homogenizing the liquid reaction mixture. For instance, a tubular stirrer can be combined with another stirrer, for example with a propeller stirrer. High intensity gas dispersion means and mixers of this type are known to a person skilled in the art, for example from Ullman's Encyclopedia of Industrial Chemistry, 5th Ed., Vol. B2 (1988), 25-21 et seq.

Normally, the process according to the invention is carried out by first charging the aryl bromide, the base, the palladium catalyst and optionally a phosphine of the formula (V) and/or a cocatalyst, a solvent (diluent) also being used if non-liquid reaction components are present, and then acetylene is introduced at a temperature within the given range into the reaction mixture using a high intensity gas dispersion means. However, the charging sequence of the abovementioned reactants before introduction of the acetylene is not crucial and can be carried out in various ways. The reaction of the process according to the invention is not sensitive to water so that it is not especially necessary to take care to exclude water. It has proved to be advantageous to place the preliminary charge of the abovementioned reactants under a protective gas such as nitrogen before introducing the acetylene. The progress of the reaction can be monitored simply by thin-layer chromatography or gas chromatography. In many cases, the diaryl-acetylene is precipitated as reaction product from the liquid reaction mixture. Furthermore, the salt formed from the base and the eliminated hydrogen bromide is often insoluble in the reaction mixture. The working-up procedure is carried out in accordance with conventional methods which are known to a person skilled in the art. For instance, the precipitated reaction product (diarylacetylene and precipitated salt if present) can be separated from the liquid phase of the reaction mixture by decanting, filtering off or centrifuging. The salt can then be separated from the diaryl-acetylene by treatment with water. If appropriate, the diaryl-acetylene can be further purified by recrystallization or column chromatography. The separated liquid phase of the reaction mixture can be reused for the next batch. However, it is also possible to separate the solvent (diluent) and the catalytically active components by distillation of the separated liquid phase and to separately recycle and again work up the respective components.

The process according to the invention allows the preparation of symmetrical diaryl-acetylenes in high yield and high selectivity in only a single reaction step, starting from readily accessible aryl bromides, and is consequently demonstrably superior to the hitherto known processes.

EXAMPLES

Example 1

4,4'-bis(carboethoxy)tolane 343.5 g of ethyl 4-bromobenzoate, 10.5 g of (P-phenyl$_3$)$_2$.PdCl$_2$, 10.5 g of copper(I) iodide, 63 g of triphenyl phosphine and 600 ml of piperidine were first charged under nitrogen in the presence of 600 ml of acetonitrile. Then, while introducing acetylene into the reaction mixture via a tubular stirrer, the temperature was increased to about 80° C. The introduction of acetylene was continued until the ethyl 4-bromobenzoate had been completely converted. Then the reaction mixture was allowed to cool and the reaction product which had crystallized out was filtered off under suction. This gave 221 g (91%) of 4,4'-bis(carboethoxy)tolane having a m.p. of 151°–153° C. The product can be further purified by recrystallization (for example from toluene) or by filtration over silica gel.

The examples 2–15 describe the preparation of various diarylacetylenes using the process according to the invention in a manner similar to Example 1.

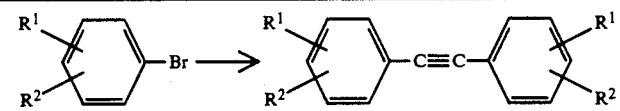

| No. | R$^1$ | R$^2$ | Base[1)] | Diarylacetylene M.p. [°C.] | Yield [%] |
| --- | --- | --- | --- | --- | --- |
| 2[2)] | H | p-COOC$_2$H$_5$ | Piperidine | 151–153 | 86 |
| 3 | H | p-COOC$_2$H$_5$ | Pyrrolidine | 151–153 | 79 |
| 4 | H | p-COOC$_2$H$_5$ | Aza-cyclo-heptane | 151–153 | 83 |
| 5 | H | p-COOC$_2$H$_5$ | DBU | 151–153 | 67 |
| 6 | H | p-COOC$_2$H$_5$ | DBN | 151–153 | 55 |
| 7 | H | p-COOC$_2$H$_5$ | DABCO | 151–153 | 59 |
| 8 | H | p-COOtC$_4$H$_9$ | Piperidine |  | 90 |
| 9 | m-COOC$_2$H$_5$ | H | Piperidine | 84–89 | 73 |
| 10 | H | p-$\overset{O}{\overset{\|}{C}}$CH$_3$ | Piperidine | 195–196 | quant. |
| 11 | m-COOCH$_3$ | p-COOCH$_3$ |  | 130–132 | 81 |

-continued

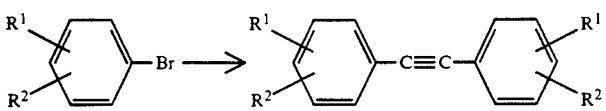

| No. | R¹ | R² | Base[1] | Diarylacetylene M.p. [°C.] | Yield [%] |
|---|---|---|---|---|---|
| 12 | H | p-C₆H₅ | Piperidine | 236–237 | 87 |
| 13 | H | p-CH=CH-C₆H₄-COOtC₄H₉ | Piperidine | >280° C.[3] | 98 |
| 14 | H | p-SO₂-C₆H₄-Cl | Piperidine | >280° C.[3] | 87 |
| 15 | H | p-CO-C₆H₄-F | Piperidine | 222–224 | 64 |
| 16 | H | p-C₆H₄-COOC₂H₅ | Piperidine | >280° C.[3] | 88 |

[1] 0.8 mol relative to 0.2 mol of aryl bromide used
[2] Cu(II) acetate monohydrate instead of Cu(I) iodide
[3] Characterized by mass spectrometry

What is claimed is:

1. A process for the preparation of symmetrical diarylacetylenes of the formula

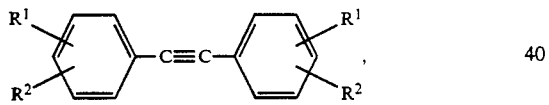

in which
R¹ is hydrogen, straight-chain or branched $C_1$–$C_8$-alkyl, $C_3$–$C_8$-cycloalkyl, phenyl, $C_7$–$C_{10}$-aralkyl, straight-chain or branched $C_1$–$C_8$-alkoxy, phenoxy, benzyloxy, β-phenyl-ethenyl, phenyl-ethinyl, phenyl-sulphonyl, phenyl-carbonyl, hydroxyl in free or protected form, fluorine, chlorine, nitro, cyano, $COR^3$, $NR^4R^5$ or $CONR^4R^5$ and
R² represents hydrogen, straight-chain or branched $C_1$–$C_8$-alkyl, fluorine, chlorine, cyano, $COR^3$ or $CONR^4R^5$ and
R¹ and R², if they are adjacent, may together form a dicarboxylic acid anhydride group,
where
R³ is hydrogen, hydroxyl, straight-chain or branched $C_1$–$C_8$-alkyl, straight-chain or branched $C_1$–$C_8$-alkoxy, phenyl or phenoxy and
R⁴ and R⁵, independently of one another, represent hydrogen or straight-chain or branched $C_1$–$C_8$-alkyl and R⁴ may also be $C_2$–$C_4$-alkoxycarboxyl or $C_2$–$C_4$-acyl,
and
it being possible for the benzene rings in the radicals R¹ and R² for their part to be substituted by straight-chain or branched $C_1$–$C_8$alkyl, straight-chain or branched $C_1$–$C_8$-alkoxy, fluorine, chlorine or $COR^3$,
which comprises reacting an aryl halide with acetylene in the presence of a palladium catalyst and a base, the acetylene being introduced into the liquid reaction mixture using a high intensity gas dispersion means, the aryl halides being aryl bromides of the formula

and the base being a nitrogen containing heterocyclic compound.

2. The process of claim 1, wherein the aryl bromide used is one of the formula

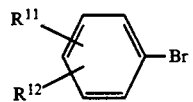

in which
R¹¹ is hydrogen, straight-chain or branched $C_1$–$C_8$-alkyl, phenyl, benzyl, straight-chain or branched $C_1$–$C_8$-alkoxy, phenoxy, benzyloxy, β-phenylethenyl, phenyl-sulphonyl, phenyl-carbonyl, fluorine, chlorine, nitro, cyano, $COR^{13}$ or $NR^{14}R^{15}$ and
R¹² represents hydrogen, straight-chain or branched $C_1$–$C_8$-alkyl, fluorine, chlorine, cyano or $COR^{13}$ and R$^{11}$ and R$^{12}$, if they are adjacent, may together form a dicarboxylic acid anhydride group,
where
R$^{13}$ is hydrogen, hydroxyl, straight-chain or branched C$_1$–C$_4$-alkyl or straight-chain or branched C$_1$–C$_4$-alkoxy and
R$^{14}$ and R$^{15}$, independently of one another, represent hydrogen or straight-chain or branched C$_1$–C$_4$-alkyl and R$^{14}$ may also be C$_2$–C$_4$-acyl,
and
it being possible for the benzene rings in the radicals R$^{11}$ and R$^{12}$ for their part to be substituted by straight-chain or branched C$_1$–C$_4$-alkyl, straight-chain or branched C$_1$–C$_4$-alkoxy, fluorine, chlorine or COR$^{13}$.

3. The process of claim 2, wherein the aryl bromide used is one of the formula

in Which
R$^{21}$ is hydrogen, straight-chain or branched C$_1$–C$_4$-alkyl, phenyl, β-phenyl-ethenyl, phenyl-sulphonyl, phenyl-carbonyl, fluorine, chlorine, cyano or COR$^{23}$ and
R$^{22}$ represents hydrogen, methyl, ethyl, cyano or COR$^{23}$ and
R$^{21}$ and R$^{22}$, if they are adjacent, may together form a dicarboxylic acid anhydride group,
where
R$^{23}$ is hydrogen, hydroxyl, methyl, ethyl, methoxy or ethoxy and it being possible for the benzene rings in the radical R$^{21}$ for their part to be substituted by fluorine, chlorine or COR$^{23}$.

4. The process of claim 1, wherein the palladium catalyst used is composed of one or more substance(s) from the group comprising palladium black, palladium/carbon, simple inorganic and organic palladium salts, complexed inorganic and organic palladium salts in which the complexing agent is benzonitrile, C$_1$–C$_4$-alkyl nitrile, triphenylarsine or a phosphine of the formula

P(R$^6$R$^7$R$^8$)

in which
R$^6$, R$^7$ and R$^8$, independently of one another, are straight-chain or branched C$_1$–C$_4$-alkyl or phenyl, it being possible for phenyl to be substituted by straight-chain or branched C$_1$–C$_4$-alkyl or C$_1$–C$_4$-alkoxy or by fluorine, chlorine or bromine,
phenyl-palladium-diphosphine iodide or palladium-tetraphosphine, in the last two cases a phosphine of the abovementioned type being used, di-(dibenzylideneacetone)palladium or di-(1,1-bis[diphenylphosphine]ferrocene)palladium dichloride, dibromide or diiodide.

5. The process of claim 4, wherein the palladium catalyst used is composed of one or more substance(s) from the group comprising organic palladium salts, complexed inorganic and organic palladium salts in which the complexing agent is a phosphine of the type of claim 4, or palladium-tetraphosphine containing a phosphine of the type of claim 4.

6. The process of claim 1, wherein the palladium catalyst is used in an amount of 0.0005–5 mol-%, relative to the aryl bromide.

7. The process of claim 6, wherein the palladium catalyst is used in an amount of 0.05–2 mol-%, relative to the aryl bromide.

8. The process of claim 1, wherein the palladium catalyst is activated by the addition of one or more phosphine(s) of the formula

P(R$^6$R$^7$R$^8$)

in which
R$^6$, R$^7$ and R$^8$, independently of one another, are straight-chain or branched C$_1$–C$_4$-alkyl or phenyl, it being possible for phenyl to be substituted by straight-chain or branched C$_1$–C$_4$-alkyl or C$_1$–C$_4$-alkoxy or by fluorine, chlorine or bromine,
in an amount of 100–2000 mol-%, relative to the palladium catalyst.

9. The process of claim 1, wherein to the palladium catalyst is (are) added one or more copper salt(s) as cocatalysts in an amount of 50–1000 mol-%, relative to the palladium catalyst.

10. The process of claim 9, wherein the copper salt(s) is (are) one or more of the group of the copper halides and copper acetate.

11. The process of claim 10, wherein the copper salt is Cu(I)iodide or Cu(II)acetate monohydrate.

12. The process of claim 1, wherein the reaction is carried out at 0°–160° C.

13. The process of claim 1, wherein the reaction is carried out in one or more solvents (diluents) present in an amount of 80–2000% by weight, relative to the amount of aryl bromide, the solvent (diluent) being selected from the group comprising hydrocarbons, ethers, alcohols, chlorinated hydrocarbons, nitriles, amides and sulphoxides, and it furthermore being possible to use excess base, as long as this is a liquid, as the solvent (diluent).

14. The process of claim 1, wherein the high intensity gas dispersion means used for the acetylene is a surface aerator or a volume aerator, it being possible to homogenize the reaction mixture by means of an additional mixer.

15. The process of claim 14, wherein the high intensity gas dispersion means used is a volume aerator.

16. The process of claim 15, wherein the high intensity gas dispersion means used is a tubular stirrer.

17. The process of claim 1, wherein the base is triethylene diamine, diazabicyclo-nonene, diaz-bicyclo-undecene or a nitrogen containing compound of the formula

N(R$^{19}$R$^{20}$R$^{17}$)

wherein
R$^{19}$ and R$^{20}$ together are C$_4$–H$_8$-alkylene, wherein in the alkylene chain one carbon atom may be replaced by an oxygen atom or the group —NR$^{17}$—, and
R$^{17}$ is hydrogen, methyl or ethyl, or triethylene diamine, diaza-bicyclo-nonene or diaza-bicyclo-undecene.

18. The process of claim 17, wherein the base is used in an amount of 95–400 mol-%, relative to the aryl bromide.

* * * * *